US007531302B1

(12) United States Patent
Drewe et al.

(10) Patent No.: US 7,531,302 B1
(45) Date of Patent: May 12, 2009

(54) NUCLEIC ACID DETECTION METHOD BY TRIPLE HELIX FORMATION

(75) Inventors: Lisa Joanne Drewe, Salisbury (GB); Gale Brightwell, Salisbury (GB); Elizabeth Ann Howlett Hall, Salisbury (GB)

(73) Assignee: Her Majesty the Queen in right of Canada, as represented by The Secretary of State for Defense in Her Brittanic Majesty's Government of the United Kingdom of Great Britain and Northern Ireland, Farnborough, Hampshire (GB)

( * ) Notice: Subject to any disclaimer, the term of this patent is extended or adjusted under 35 U.S.C. 154(b) by 0 days.

(21) Appl. No.: 09/744,489

(22) PCT Filed: Jul. 19, 1999

(86) PCT No.: PCT/GB99/02317

§ 371 (c)(1),
(2), (4) Date: Jan. 23, 2001

(87) PCT Pub. No.: WO00/05408

PCT Pub. Date: Feb. 3, 2000

(30) Foreign Application Priority Data

Jul. 23, 1998 (GB) .................................. 9815933.8

(51) Int. Cl.
*C12Q 1/68* (2006.01)
*C12P 19/34* (2006.01)
*C07H 21/04* (2006.01)

(52) U.S. Cl. ...................... 435/6; 435/91.2; 536/24.31; 536/24.32; 536/24.33

(58) Field of Classification Search ..................... 435/6, 435/7.1, 91.1, 91.2, 287.2; 536/22.1, 23.1, 536/24.3–24.33
See application file for complete search history.

(56) References Cited

U.S. PATENT DOCUMENTS 5,641,625 A * 6/1997 Ecker et al. ..................... 435/6
5,723,591 A * 3/1998 Livak et al. ................. 536/22.1
5,800,984 A * 9/1998 Vary .............................. 435/6

6,165,720 A * 12/2000 Felgner et al. ................. 435/6
6,485,901 B1 11/2002 Gildea et al.

FOREIGN PATENT DOCUMENTS

| WO | WO 92/11390    |   | 7/1992 |
|----|----------------|---|--------|
| WO | WO 9602558 A1  | * | 2/1996 |
| WO | WO 9705280 A1  | * | 2/1997 |
| WO | WO 97/14793    |   | 4/1997 |
| WO | WO99/21881     | * | 5/1999 |

OTHER PUBLICATIONS

Seeger et al. PNA-mediated purification of PCR amplifiable human genomic DNA from whole blood. Biotechniques, vol. 23, No. 3, pp. 512-514, 516, 517, 1997.*
Kai e, et al. Novel DNA detection system of flow injection analysis (2). The distinctive properties of a novel system employing PNA (peptide nucleic acid) as a probe for specific DNA detection. Nucleic Acid Symposium series No. 37, p. 321-322, 1997.*
Armitage et al. Peptide nucleic acid-anthraquinone conjugates: strand invasion and photoinduced cleavage of duplex DNA. Nucleic Acids Res., vol. 25, No. 22, pp. 4674-4678, 1997.*
Orum et al. Single base pair mutation analysis by PNA directed PCR clamping. Nucleic Acids res., vol. 21, No. 23, pp. 5332-5336, 1993.*
Kai, et al., "Novel DNA detection system of flow injection analysis (2): The distinctive properties of a novel system employing PNA (peptide nucleic acid) as a probe for specific DNA detection," *Nucleic Acids Symposium Series*, vol. 37, pp. 321-325 (1997).
Seeger, et al., "PNA-Mediated Purification of PCR Amplifiable Human Genomic DNA from Whole Blood," *Biotechniques*, vol. 23, No. 3, pp. 512-514, 516, 517 (Sep. 1, 1997).
Wang, et al., "Peptide nucleic acids probes for sequence-specific DNA biosensors" *Journal of the American Chemical Society*, vol. 118, No. 33, pp. 7667-7670 (Aug. 21, 1996).
Sawata, Shinya et al.; "Application of peptide nucleic acid to the direct detection of deoxyribonucleic acid amplified by polymerase chain reaction"; *Biosensors & Bioelectronics*; 14 (1999) pp. 397-404.

* cited by examiner

*Primary Examiner*—Suryaprabha Chunduru
(74) *Attorney, Agent, or Firm*—Kilpatrick Stockton LLP

(57) ABSTRACT

A method for detecting the presence of a target nucleic acid sequence in a sample, the method comprising (a) amplifying the target nucleic acid so that the product of the amplification reaction includes a purine rich region, (b) contacting the sample during the amplification with a peptide nucleic acid able to bind to at least a portion of the target sequence; and (c) detecting the presence of triplex DNA structures. The detection is suitably effected directly, for example using a surface plasmon resonance detector.

10 Claims, 2 Drawing Sheets

DNA duplex → PNA-DNA duplex D-loop (1:1) → PNA$_2$-DNA triplex D-loop (2:1)

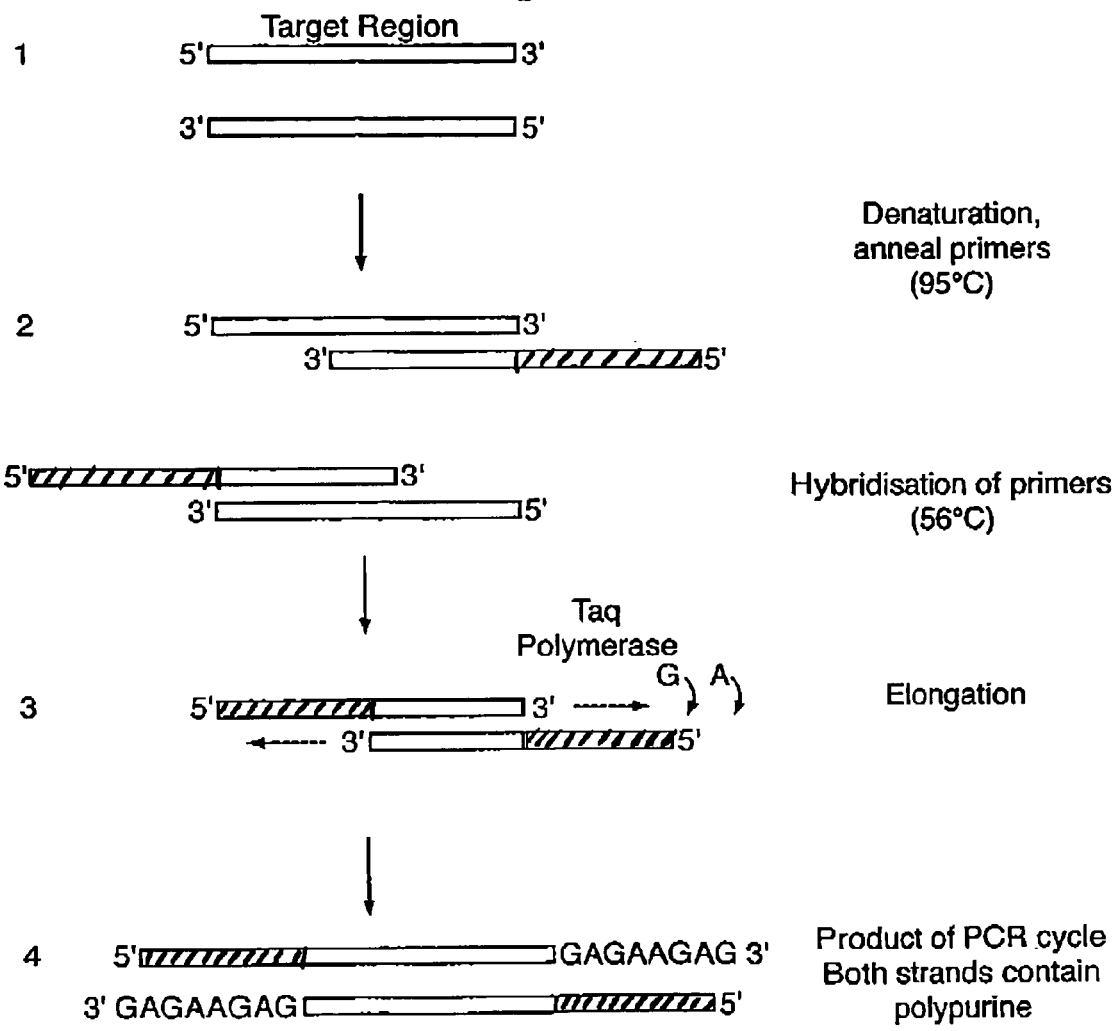

SEQUENCE LISTING

<160> NUMBER OF SEQ ID NOS: 4

<210> SEQ ID NO 1
<211> LENGTH: 82
<212> TYPE: DNA
<213> ORGANISM: Artificial Sequence

```
<220> FEATURE:
<223> OTHER INFORMATION: PCR product

<400> SEQUENCE: 1
ataaatacaa ccaacaaaat aaatagtcat aaaattgtat acattagcaa tgcataccac      60
aaagttctaa gtactaaaat at                                              82

<210> SEQ ID NO 2
<211> LENGTH: 185
<212> TYPE: DNA
<213> ORGANISM: Artificial Sequence
<220> FEATURE:
<223> OTHER INFORMATION: PCR Product

<400> SEQUENCE: 2
gcgaaacgga acatagccca aaccaagagg cttgcctctt ggggttgtag gacattctat      60
acggagttac aaaggaagca ggtagacgaa gcgacctgga aaggtccgtc gtagagggta    120 acaacccgt agtcgaaact tcgttctctc ttgaatgtat cctgagtacg gcggaacacg     180
tgaaa                                                                185

<210> SEQ ID NO 3
<211> LENGTH: 15
<212> TYPE: DNA
<213> ORGANISM: Artificial Sequence
<220> FEATURE:
<223> OTHER INFORMATION: Peptide nucleic acid

<400> SEQUENCE: 3
ttttccttcc ctttt                                                      15

<210> SEQ ID NO 4
<211> LENGTH: 15
<212> TYPE: DNA
<213> ORGANISM: Artificial Sequence
<220> FEATURE:
<223> OTHER INFORMATION: Peptide nucleic acid

<400> SEQUENCE: 4
ttttcccttc ctttt                                                      15
```

NUCLEIC ACID DETECTION METHOD BY TRIPLE HELIX FORMATION

This application claims priority to Great Britain Application No. 9815933.8 filed on Jul. 23, 1998 and International Application Publication Number WO/00/05408 filed on Jul. 19, 1999.

BACKGROUND OF THE INVENTION

1. Field of the Invention

The present invention relates to a method of detecting specific target DNA sequences, and in particular to the products of amplification reactions, as well as to reagents and apparatus used in that method.

2. Description of the Related Art

Many methods are known in order to detect the presence of particular target DNA sequences in a sample. A substantial proportion of these methods require that the DNA is denatured to single stranded form and then this sequence is hybridised or otherwise allowed to bind to a labelled sequence specific probe.

The target sequences are frequently subjected to amplification reactions, for example the polymerase chain reaction or the ligase chain reaction, in order to increase the amount of the target sequence to detectable levels.

Other methods of detecting sequences include the use of intercalating dyes which are incorporated into the sequences during the amplification reaction. However such methods are relatively non specific as the dyes will intercalate with any amplification product, even if they are the result of non-specific amplification products.

Other assays such as the TAQMAN™ assay utilise complex probes which include reporter and quencher moieties during the course of the amplification process. These probes hybridise to single stranded target sequences during the amplification reaction and are then digested by the enzymes carrying out the reaction. The relationship between quencher and reporter molecule of the probe produces a signal which can be monitored. The probes used in this case however, are complex and expensive.

It is known that peptide nucleic acids will strand invade DNA at purine rich sites to form triplex structures (P. E. Nielson et al., Science, 1991, 254, p 1497-1506, Turney D. Y. et al., Proc. Natl. Acad. Sci. USA, 1993, 90, 1667-1670). The mechanism by which this is effected is illustrated diagrammatically hereinafter in FIG. 1.

The applicants have found that this phenomenon can be used in detection of target DNA sequences.

SUMMARY OF THE INVENTION

A method for detecting the presence of a target nucleic acid sequence in a sample, said method comprising
  (a) amplifying said target nucleic acid so that the product of the amplification reaction includes a purine rich region,
  (b) contacting the sample with a peptide nucleic acid able to bind to at least a portion of said target sequence; and
  (c) detecting the presence of triplex DNA structures.

The method enabling the direct detection of target sequences, for example amplification products without the usual denaturation step required for duplex formation with a nucleic acid probe.

The expression "purine rich region" means that the sequence is suitable for strand invasion by a peptide nucleic acid (PNA). Such regions suitably contain at least four consecutive purine residues.

The reaction in step (a) above is suitably effected in the presence of a buffer, and preferably a low salt buffer for example containing 50 mM or less of salt as this favours triplex formation as compared to DNA:DNA duplexes. Furthermore, the pH of the buffer used will depend on the precise nature of the PNA employed. If C's are used in the PNA strand to strand invade G's on duplex DNA, careful consideration has to be given to the pH of the buffer as the C involved in forming the Hoogsteen base-pair needs to be protonated, requiring a buffer of low pH, for example of less than 4.5.

The peptide nucleic acid used in the method of the invention may be single stranded or it may be bis-PNA. Preferably, the peptide nucleic acid used in the method is a bis-PNA as this results is a faster strand invasion process and a more stable triplex product.

Bis-PNA will comprise of two anti-parallel strands joined by a hydrophilic linker. One strand will be designed for Watson-Crick recognition of DNA within the target sequence, and the other strand is designed for Hoogsteen recognition of a PNA-DNA duplex. Such acids will be optimal for $PNA_2DNA$ triplex stability and thus enhance strand-displacement binding to double-stranded DNA.

Peptide nucleic acids used will suitably contain a sequence of poly-T's or poly-C's.

The target nucleic acid is first subject to an amplification reaction such as the polymerase chain reaction (PCR) or ligase chain reaction (LCR), preferably PCR. The product may be exposed to the peptide nucleic acid during or after the amplification reaction, but is preferably exposed to the peptide nucleic acid after completion of the amplification reaction.

Where the target nucleotide sequence contains or is selected such that it contains a purine rich region, the method can be carried out directly. Where such regions do not exist in the target sequence, they may be introduced during the amplification reaction. In this case, the amplification will be effected using one or more primers which comprise a plurality of pyrimidines, suitably at the 5' end thereof. This region will chain extend during the extension phase of the amplification (as illustrated in FIG. 2 hereinafter). The 3'-end of both amplified strands of the amplification obtained using these primers should now contain the purine rich sites. Indeed, PCR products, that were tagged in this manner, have been cloned and sequenced and were found to have the poly-purine stretches incorporated at their 3'end. This ensures that a suitable PNA binding purine rich region is contained within the amplification product.

Primers of this sort form a further aspect of the invention.

The triplex formed may be detected using various methods in step (b). For example, gel retardation methods may be used. When the product is subjected to gel electrophoresis, for instance on a non-denaturing polyacrylamide gel, and then stained using conventional reagents such as ethidium bromide, the presence of a retarded triplex fraction can be observed.

This method however is relatively slow. Furthermore, comparison with a similar sequence which is not in the form of a triplex is required as a standard.

Preferably therefore, the detection is effected using a capture assay. The capture agent in this case is suitably the PNA sequence which is immobilised on a support. The sample is then contacted with the support whereupon any target sequence present will become associated with the PNA on the surface. It can then be detected using any of the known techniques.

In a particularly preferred embodiment, the support is a waveguide of a detection device which operates using evanescent wave detection. An example of such a device is a surface plasmon resonance detector. This allows the direct and rapid detection of target nucleotide sequence within a sample.

Thus a product of the amplification reaction is simply allowed to flow over the waveguide of such a detector and the presence of an amplicon can be detected in something approaching "real time".

In a further aspect, the invention provides a kit for use in the method of the invention. These kits suitably comprise a PNA designed to form a triplex with a target DNA. Optionally also, it may contain primers which can be used in the amplification of the target DNA, in particular primers which are 5'-tagged with pyrimidines.

The kit may also comprise a waveguide of a evanescent wave detector and particularly a surface plasmon resonance detector having supported thereon, the peptide nucleic acid which specifically binds a target DNA sequence.

The invention will now be particularly described by way of example with reference to the accompanying diagrammatic drawings in which:

BRIEF DESCRIPTION OF THE DRAWINGS

FIG. 2 illustrates diagrammatically the incorporation of purine rich regions into an amplification product, using 5'-tagging of primers with polypyrimidine sequences;

DETAILED DESCRIPTION OF THE INVENTION

Example 1

Triplex Formation

Figure 1:
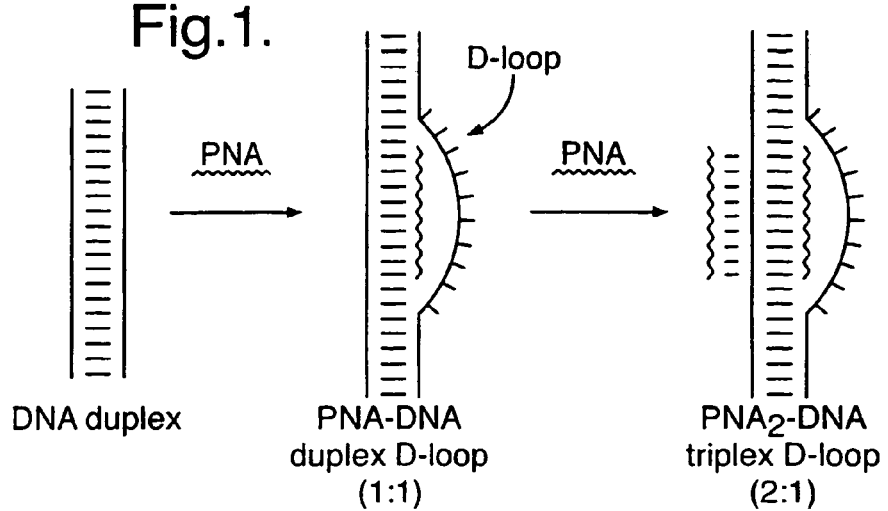
FIG. 1 illustrates diagrammatically PNA:DNA triplex formation.

The ability of PNA to form triplex structures with PCR products has been demonstrated using gel retardation studies. Two PCR products were chosen for study. One has a sequence capable of forming triplexes with a PNA probe i.e. contains poly-A sites.

PCR82
5'
ATAAATACAACCAACAAAATAAATAGT-
CATAAAATTGTATACATTAGCAATGCATACC
ACAAAGTTCTAAGTACTAAAATAT 3' (SEQ ID NO 1)

The other does not contain poly-A sites and acts as a negative control.

PCR 175
5'
GCGAAACGGAACATAGCCCAAACCAA-
GAGGCTTGCCTCTTGGGGTTGTAGGACATTCT
ATACGGAGTTACAAAGGAAGCAGGTA-
GACGAAGCGACCTGGAAAGGTCCGTCG-
TAGAGGGTAAC AACCCCGTAGTCGAAACT-
TCGTTCTCTCTTGAATGTATCCTGAGTACGGCG
GAACACGTGAAA
3' (SEQ ID NO 2)

Two types of PNA probe were used, one was a linear sequence and contains a sequence of poly-T's

PNA057

N TTTTCCTTCCCTTTT C (SEQ ID NO 3)

The other, a bis-PNA of the same linear sequence but composed of two anti-parallel strands joined by a hydrophilic linker. One strand was designed for Watson-Crick recognition of DNA and the other strand is designed for Hoogsteen recognition of a PNA-DNA duplex and should be optimal for $PNA_2DNA$ triplex stability and thus enhance strand-displacement binding to double-stranded DNA.

PNA058

N TTTTCCCTTCCTTTT LLL TTTTCCTTCCCTTT C
  (SEQ ID NO 4)         (SEQ ID NO 3)

Each PCR product (5 μg/ml) was incubated with each PNA probe (10 μg/ml), at 37° C. in 0.5×TE buffer (1 mM Tris.HCl, 0.1 mM EDTA, 5 mM NaCl, pH 8.0) for varying time intervals before the reaction was terminated by adding 150 mM HBS, pH 7.4 on ice. Samples were run on a non-denaturing 12% polyacrylamide gel. The electrophoretic mobility of the triplex $PNA_2DNA$ was compared to the duplex DNA of the relevant PCR product and visualised by EtBr staining. Triplex structures were observed suggesting that PNA can directly detect double-stranded PCR products.

The results of the gel retardation studies showed that single-stranded PNA did not strand invade the PCR products within the first 60 minutes. (This is backed up in the literature where it has been demonstrated that the association of a bis-PNA with a single strand of homopurine DNA gives a complex that is significantly more stable than the one formed with two single PNA strands due to a more favourable entropy of reaction.)

Bis-PNA, however, formed a triplex within the first 10 minutes of reaction.

Example 2

Detection of Triplexes on a Surface Plasmon Resonance (SPR) Surface

Figure 3:
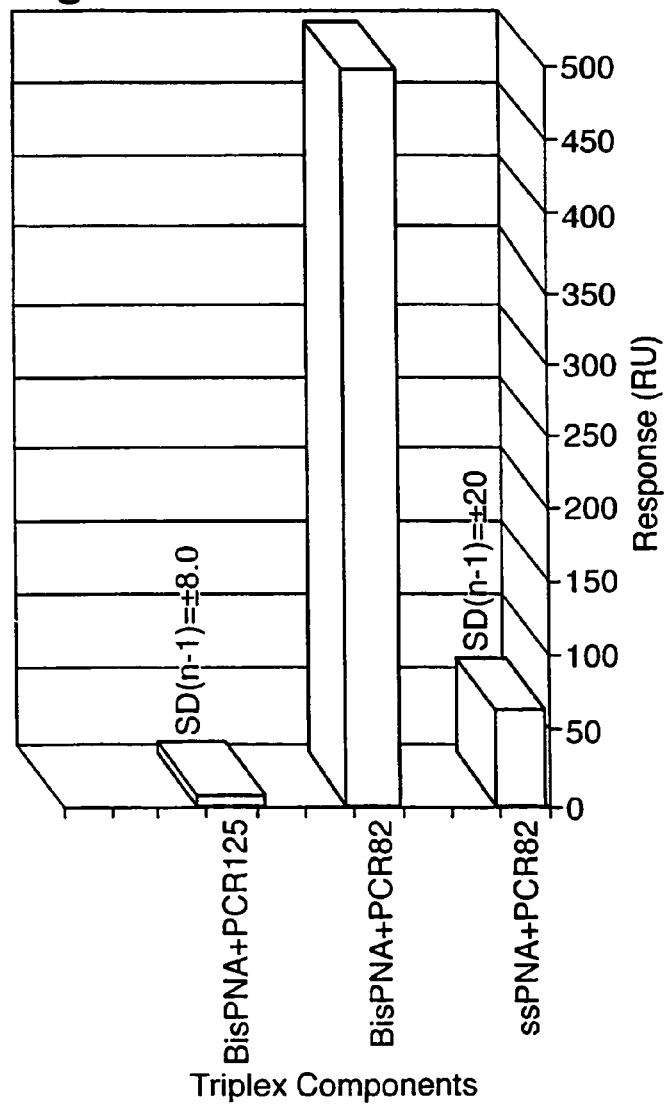
FIG. 3 illustrates triplex formation on the surface of a surface plasmon resonance detector.

Biotin labeled bis-PNA (50 μg/ml) was linked to a dextran surface (Biacore, SAchip) via a streptavidin-biotin interaction. A sample of both PCR products (10 μg/ml), in water, was flowed over this sensor surface and were detected by a change in refractive index. The SPR system could differentiate between purine-rich and non-purine rich PCR products in near real time (See FIG. 3).

The invention claimed is:

1. A method for detecting the presence of a target nucleic acid sequence in a sample, said method comprising:

(a) amplifying said target nucleic acid and introducing a purine rich region into the target sequence during amplification, wherein the resulting target sequence is able to bind a peptide nucleic acid, and contacting the sample during the amplification with a support on which is immobilized a bis-peptide nucleic acid able to bind at least a portion of the target sequence, wherein the portion comprises the purine rich region introduced during amplification; and (b) detecting the presence of triplex structures resulting from the binding of the amplified target sequence to the bis-peptide nucleic acid, wherein the detection of the presence of triplex structures indicates the presence of target nucleic acid sequence in the sample.

2. The method according to claim 1 wherein the amplification reaction is a polymerase chain reaction.

3. The method according to claim 1 wherein primers used in the amplification comprise a plurality of pyrimidines at the 5' end thereof.

4. The method according to claim 1 wherein the support is a waveguide of a detection device.

5. The method according to claim 4 wherein the detection device is a surface plasmon resonance detector.

6. A method for detecting the presence of a target nucleic acid sequence in a sample, comprising (a) amplifying the target nucleic acid so that the product of the amplification reaction includes a purine rich region, and contacting the sample with a waveguide of an evanescent waveguide detector on which is immobilized a bis-peptide nucleic acid able to bind at least a portion of the target sequence, wherein the portion comprises the purine rich region included in the product of the amplification reaction; and (b) detecting the presence of triplex structures formed by the product of the amplification reaction and the bis-peptide nucleic acid on the waveguide using the detector.

7. The method of claim 6 wherein the evanescent waveguide detector is a surface plasmon resonance detector.

8. The method of claim 6 wherein the amplification reaction is a polymerase chain reaction.

9. A kit for detecting the presence of a target nucleic acid sequence in a sample, wherein the kit comprises:
   a) a bis-peptide nucleic acid (PNA) having a sequence that is specific for the target nucleotide sequence, wherein the target nucleotide sequence contains a purine rich region that has been introduced into the target sequence during amplification, and wherein the bis-PNA is immobilized on a waveguide of an evanescent wave detector apparatus and can form a $PNA_2DNA$ triplex structure with the purine rich region introduced into the target nucleotide sequence during amplification of the target nucleotide sequence; and,
   b) a set of amplification primers that can amplify in the presence of the bis-PNA a sequence comprising the target sequence.

10. The kit of claim 9, wherein the evanescent wave detector apparatus is a surface plasmon resonance detector.

* * * * *

UNITED STATES PATENT AND TRADEMARK OFFICE
CERTIFICATE OF CORRECTION

PATENT NO.         : 7,531,302 B1
APPLICATION NO.    : 09/744489
DATED              : May 12, 2009
INVENTOR(S)        : Lisa Joanne Drewe, Gale Brightwell and Elizabeth Ann Howlett Hall It is certified that error appears in the above-identified patent and that said Letters Patent is hereby corrected as shown below:

Title page of Patent
(73) Assignee

Delete "Her Majesty the Queen in right of Canada, as represented by The Secretary of State for Defense in Her Brittanic Majesty's Government of the United Kingdom of Great Britain and Northern Ireland"

and insert in place thereof:

--The Secretary of State for Defence--

Signed and Sealed this

Fourteenth Day of July, 2009

JOHN DOLL
*Acting Director of the United States Patent and Trademark Office*